United States Patent
Shoji et al.

(10) Patent No.: US 7,738,940 B2
(45) Date of Patent: Jun. 15, 2010

(54) MEDICAL IMAGE RECORDING SYSTEM

(75) Inventors: Hideyuki Shoji, Sagamihara (JP);
Mutsumi Ohshima, Tokyo (JP);
Yoshitaka Miyoshi, Tokyo (JP);
Tomohiko Oda, Kawagoe (JP);
Nobuyasu Ito, Tokyo (JP); Tadao Eto,
Tokyo (JP); Toshiro Ijichi, Tokyo (JP);
Katsuyoshi Ishibashi, Tokyo (JP);
Masashi Kikkawa, Tokyo (JP);
Kazutaka Nakatsuchi, Tokyo (JP)

(73) Assignee: Olympus Corporation, Tokyo (JP)

( * ) Notice: Subject to any disclaimer, the term of this patent is extended or adjusted under 35 U.S.C. 154(b) by 866 days.

(21) Appl. No.: 10/830,803

(22) Filed: Apr. 23, 2004

(65) Prior Publication Data

US 2004/0243448 A1    Dec. 2, 2004

(30) Foreign Application Priority Data

May 28, 2003  (JP)  ............................. 2003-150106
Dec. 10, 2003  (JP)  ............................. 2003-412424

(51) Int. Cl.
*A61B 5/05* (2006.01)
(52) U.S. Cl. .................. 600/407; 600/103; 600/112; 600/118; 600/160; 600/476
(58) Field of Classification Search .............. 600/117, 600/118, 160, 407, 101, 103, 112, 476
See application file for complete search history.

(56) References Cited

U.S. PATENT DOCUMENTS 4,220,999 A * 9/1980 Reichlin et al. ............. 707/102
5,209,220 A * 5/1993 Hiyama et al. ............. 600/109
5,830,121 A * 11/1998 Enomoto et al. ............ 600/117
5,865,745 A    2/1999 Schmitt et al.
5,871,439 A * 2/1999 Takahashi et al. .......... 600/118
5,967,969 A * 10/1999 Enomoto et al. ............ 600/117
6,322,496 B1   11/2001 Iida et al.

(Continued)

FOREIGN PATENT DOCUMENTS

EP    1 287 781 A1    3/2003

(Continued)

OTHER PUBLICATIONS

Australian Office Action dated May 2, 2007.

(Continued)

*Primary Examiner*—Brian Casler
*Assistant Examiner*—Joel M Lamprecht
(74) *Attorney, Agent, or Firm*—Scully, Scott, Murphy & Presser, P.C.

(57) ABSTRACT

A medical image recording system easily obtains information of a device, etc. used at the time of an examination without conscious effort on operator's part, and records image information and the device information, which are obtained at the time of the examination, by making a 1-to-1 association between them. The system comprises at least an image information obtaining unit obtaining an observation image at the time of an examination for a medical treatment, a device information obtaining unit obtaining information of a device used at the time of the examination, and a recording unit recording information composing of the image information obtained by the image information obtaining unit and the device information obtained by the device information obtaining unit, as one associated information.

12 Claims, 12 Drawing Sheets

U.S. PATENT DOCUMENTS

| | | | |
|---|---|---|---|
| 6,331,181 B1 * | 12/2001 | Tierney et al. | 606/130 |
| 6,436,032 B1 * | 8/2002 | Eto et al. | 600/117 |
| 6,638,212 B1 * | 10/2003 | Oshima | 600/109 |
| 6,712,756 B1 * | 3/2004 | Kura et al. | 600/118 |
| 6,726,620 B2 * | 4/2004 | Shibata et al. | 600/118 |
| 6,976,954 B2 * | 12/2005 | Takahashi | 600/118 |
| 6,977,670 B2 * | 12/2005 | Takahashi et al. | 348/65 |
| 2001/0044731 A1 * | 11/2001 | Coffman et al. | 705/3 |
| 2003/0046109 A1 * | 3/2003 | Uchikubo | 705/2 |

FOREIGN PATENT DOCUMENTS

| | | |
|---|---|---|
| JP | 5-336544 | 12/1993 |
| JP | 7-141498 | 6/1995 |
| JP | 7-303651 | 11/1995 |
| JP | 10-290778 | 11/1998 |
| JP | 2001-46326 | 2/2001 |
| JP | 2001-345961 | 12/2001 |
| JP | 2003-70733 | 3/2003 |
| JP | 2003-91596 | 3/2003 |
| JP | 2003-091596 | 3/2003 |

OTHER PUBLICATIONS

Office Action dated Jan. 7, 2010 issued to the corresponding European Patent Application No. 04715547.8.

* cited by examiner

| TYPE NAME INFORMATION | TYPE NAME OF ENDOSCOPE |
| | TYPE NAME OF LIGHT SOURCE DEVICE |
| | TYPE NAME OF VIDEO PROCESSOR |
| S/N INFORMATION | S/N OF ENDOSCOPE |
| | S/N OF LIGHT SOURCE DEVICE |
| | S/N OF VIDEO PROCESSOR |
| USE TIME INFORMATION | USE TIME OF ENDOSCOPE |
| | USE TIME OF LIGHT SOURCE DEVICE |
| | USE TIME OF VIDEO PROCESSOR |
| USE NUMBER INFORMATION | NUMBER OF USES OF ENDOSCOPE |
| | NUMBER OF USES OF LIGHT SOURCE DEVICE |
| | NUMBER OF USES OF VIDEO PROCESSOR |
| SETTING VALUE INFORMATION | SHOOTING CONDITION (EX. ENHANCEMENT LEVEL LIGHT CONTROL LEVEL MAGNIFICATION, ETC.) |

FIG. 2

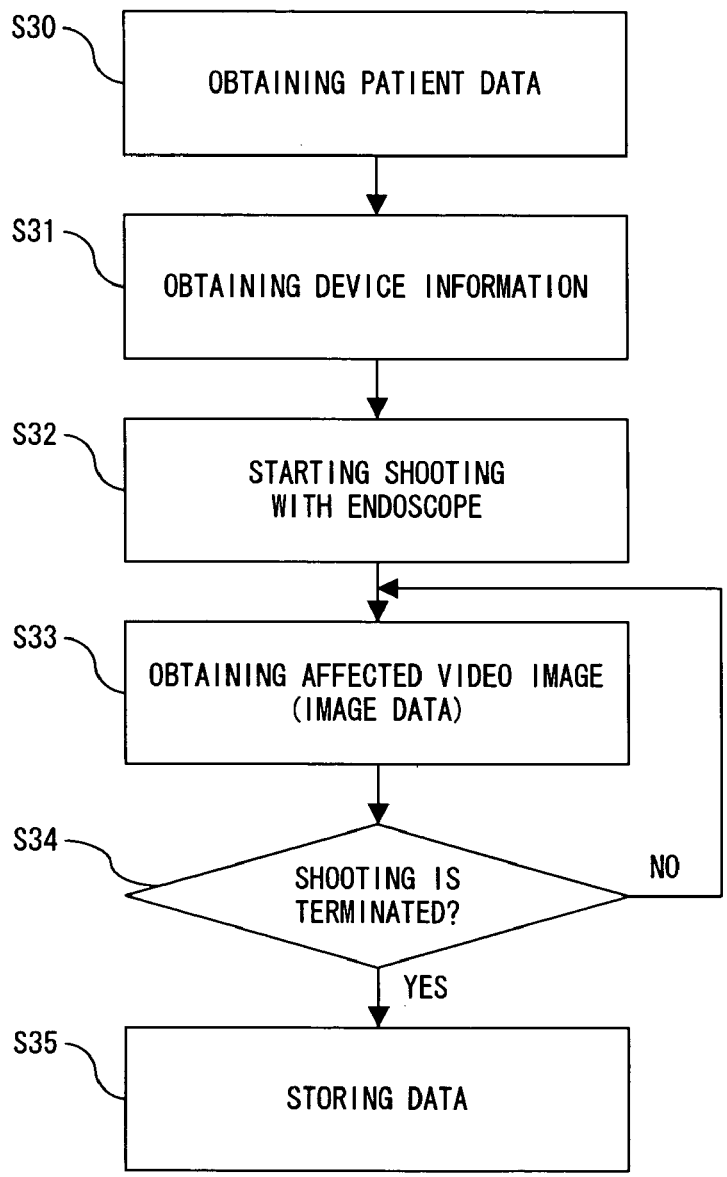
F I G. 3

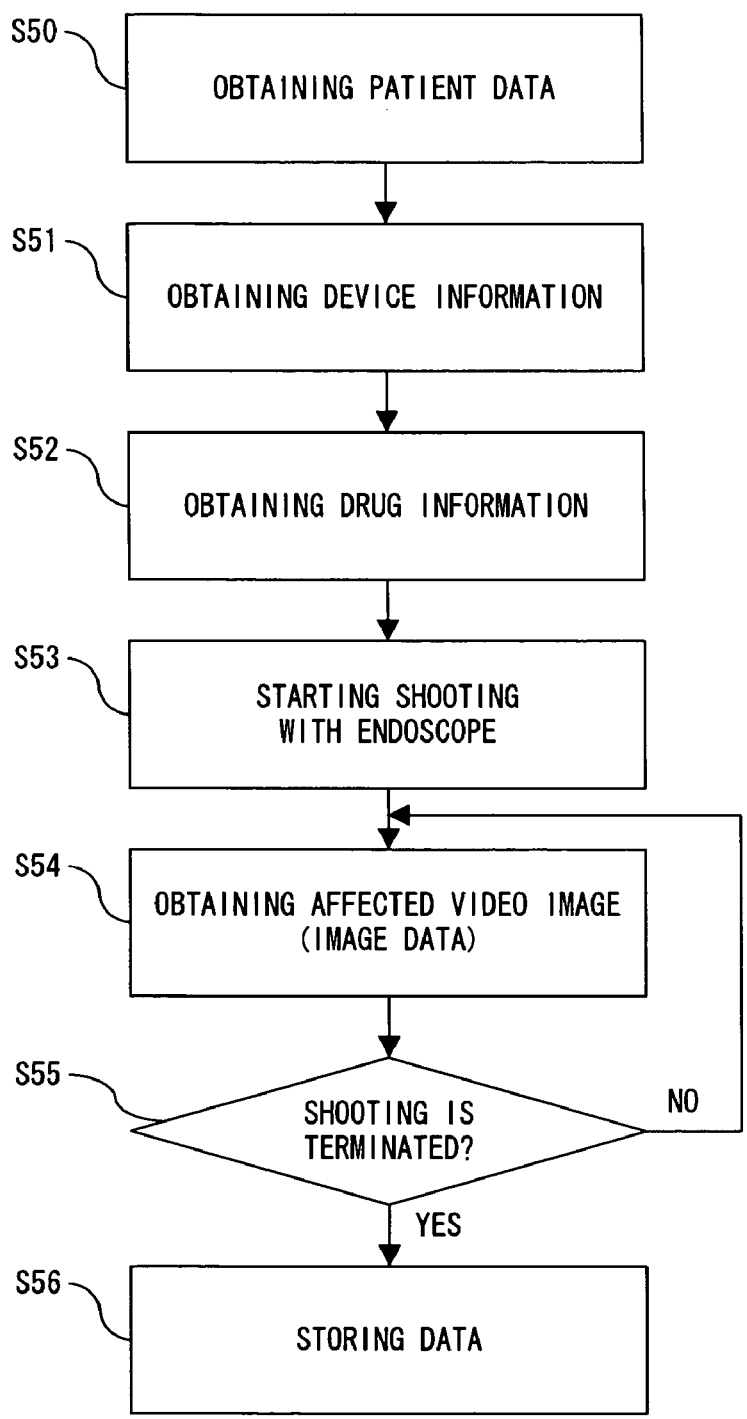
F I G. 6

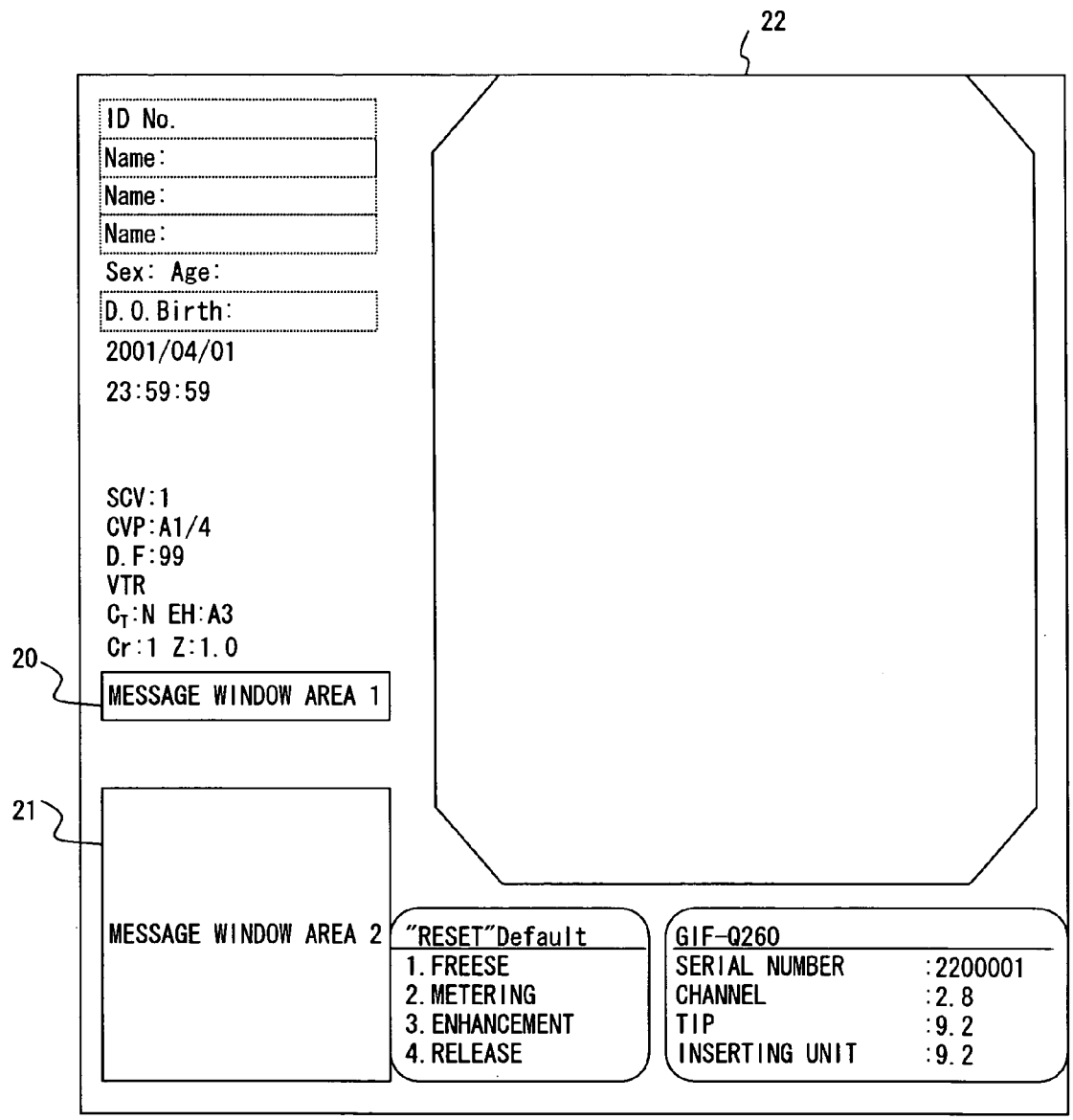
F I G. 9

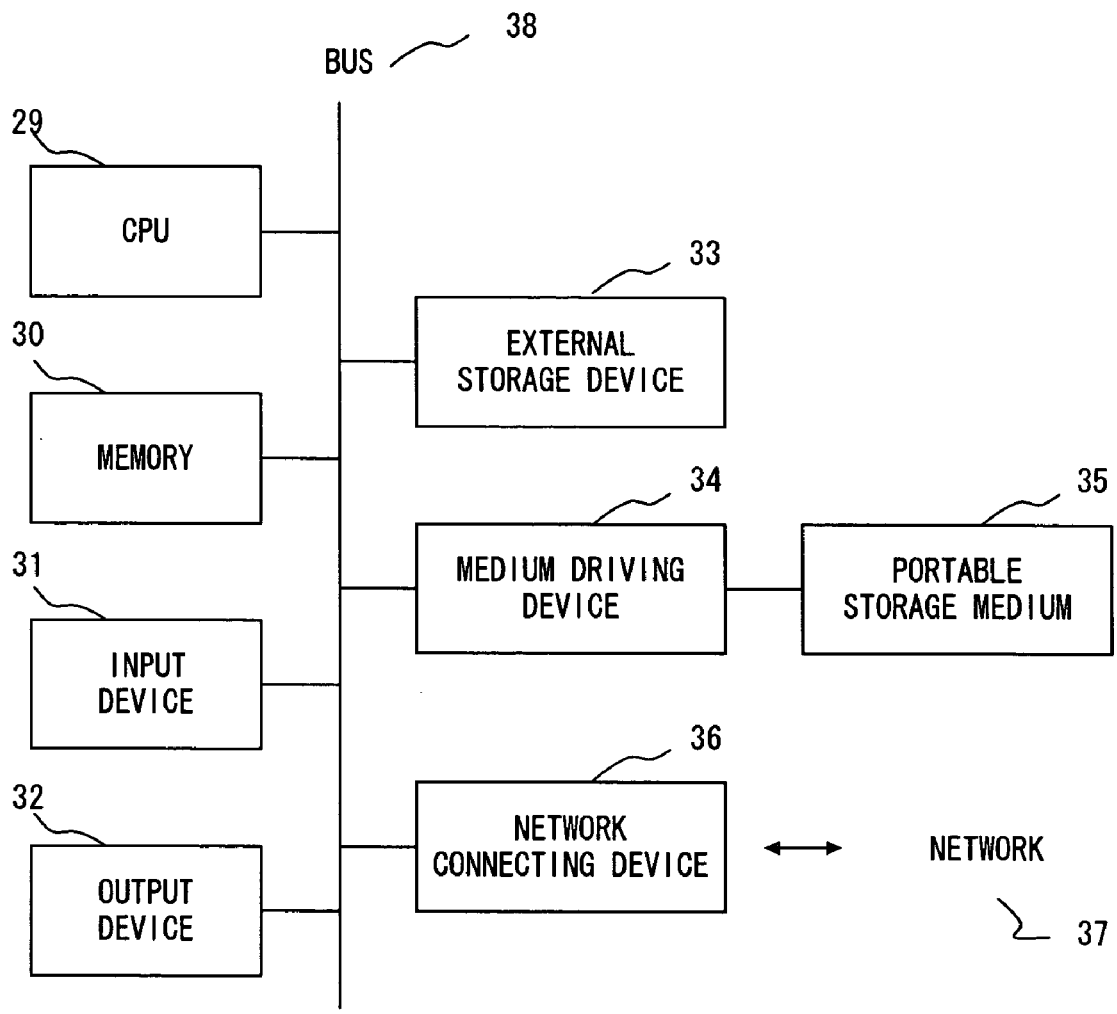
F I G. 1 2

MEDICAL IMAGE RECORDING SYSTEM

CROSS REFERENCE TO RELATED APPLICATIONS

This application is based upon and claims the benefit of priority from the prior Japanese Patent Application No. 2003-150106, filed May 28, 2003; No. 2003-412424, filed Dec. 10, 2003, the entire contents of both of which are incorporated herein by reference.

BACKGROUND OF THE INVENTION

1. Field of the Invention

The present invention relates to a medical image recording system.

2. Description of the Related Art

Conventionally, a medical image recording system which records information of an image shot by making an examination with an electronic endoscope, etc., and allows the information to be effectively used for a diagnosis after the examination, an electronic carte to be filled in, the progression observation of a treatment effect, results of examinations made by a plurality of doctors, a diagnostic conference, etc. is proposed (for example, see Japanese Patent Publication No. HEI07-141498). Also a medical image recording system having a mechanism for obtaining and recording information of a device used for an examination to grasp the use state of the device used at the time of the examination is proposed (for example, see Japanese Patent Publication No. 2001-46326).

In these medical image recording systems, an observation image of a medical device such as an electronic endoscope, etc. is recorded along with patient data (an ID number, a name, etc.), and when a report of an examination is created with an electronic carte after the examination is terminated, a shot medical image is pasted on an electronic carte report screen, contents of an examination made are recorded, and the type name and the S/N (serial number) of a device used for the examination, and the name of a drug, etc. used for the examination are input.

However, with the conventional medical image recording systems, the information of the type name, the S/N, etc. of a device used for an examination is manually input, or such information items are selected from a list preregistered to a database, in order to record the contents of an examination made.

In the case of a large hospital, examinations of as many as 10,000 patients per year can possibly be made, and various types of devices are used for only one examination. By way of example, only for an electronic endoscope, its types include a duodenal endoscope, an esophageal endoscope, an endoscope for an electric knife treatment, etc. Additionally, product generations exist even for an endoscope of the same type. For example, an endoscope introduced ten years ago and an endoscope introduced one year ago coexist, and are used in many cases.

Accordingly, input operations for recording the information (such as a type name, an S/N, etc.) of a device used for an examination to an electronic carte, etc. after the examination is made are very troublesome. Additionally, since the input operations rely on a note or memory of a user, there is a great possibility that an input error is caused. Additionally, if an input error occurs, it is difficult to notice the input error, and the error can be possibly overlooked. Furthermore, if a person who makes an examination differs from a person who makes a diagnosis after the examination, it becomes much more difficult to notice the above described error.

Besides, since a large number of examinations are made for one year as described above, the amount of image information handled becomes very large. Therefore, it is difficult to make an association between information of a shooting condition used at the time of an examination, a device, etc., and image information, after the examination is made. Furthermore, if image processes such as an enhancement, etc. are executed at the time of shooting, they can possibly hinder an image process when image information is reproduced later.

A problem of the above described conventional medical image recording systems is that a 1-to-1 association is not assured to be made (image information is not associated with the information of a device, etc. due to a man-made error) between image information obtained at the time of an examination, and information of a medical device, etc. used when an image is obtained (at the time of the examination). This is because the image information obtaining unit obtaining an observation image at the time of an examination, and the device information obtaining unit obtaining information of a medical device used when the image is obtained (at the time of the examination) are completely independent.

SUMMARY OF THE INVENTION

An object of the present invention is to implement a medical image recording system that obtains information of a device, etc. used when an image is obtained (at the time of the examination) unconsciously or easily the same time the examination is made (the same time the image information is obtained), and records the image information obtained at the time of the examination, and the information of the device, etc. used at the time of the examination by making a 1-to-1 association between the image information and the information of the device, etc., in order to overcome the above described problems posed to the conventional systems.

The invention recited in claim 1 is a medical image recording system which comprises: an image information obtaining unit obtaining an observation image at the time of an examination for a medical treatment; a device information obtaining unit obtaining information of a device used at the time of the examination; and a recording unit recording information composing of the image information obtained by the image information obtaining unit and the device information obtained by the device information obtaining unit, as one associated information.

An invention recited in claim 1 achieves a good effect in that the image information obtained by the image information obtaining unit at the time of the examination, and the information of the device used at the time of the examination obtained by the device information obtaining unit, are recorded as one associated information by the recording unit.

An invention recited in claim 2 is the medical image recording system according to claim 1, wherein the device information obtained by the device information obtaining unit, includes at least one of a type name, a serial number, a use time, the number of uses, and a setting value of the device.

The invention recited in claim 2 achieves a good effect that the image information obtained by the image information obtaining unit at the time of the examination, and the device information including at least one of the type name, the serial number, the use time, the number of uses, and the setting value of the device used at the time of the examination obtained by the device information obtaining unit, are recorded as one associated information by the recording unit.

An invention recited in claim 3 is a medical image recording system which comprises: an image information obtaining unit obtaining an observation image at the time of an examination for a medical treatment; a drug or device information obtaining unit obtaining information of a drug or a device, which is used at the time of the examination; and a recording unit recording information composing of the image information obtained by the image information obtaining unit and the drug or device information obtained by the drug or device information obtaining unit, as one associated information.

The invention recited in claim 3 achieves a good effect that the image information obtained by the image information obtaining unit at the time of the examination and the information of the drug or device used at the time of the examination obtained by the drug or device information obtaining unit, are recorded as one associated information by the recording unit.

An invention recited in claim 4 is the medical image recording system according to claim 3, wherein the drug or device information obtaining unit is an identification information reading unit reading identification information written in a drug or a device as the drug or device information obtaining unit.

The invention recited in claim 4 achieves a good effect similar to that of the invention according to claim 3 by reading the identification information written in the drug or the device by using the identification information reading unit.

An invention recited in claim 5 is a medical image recording system which comprises: an image information obtaining unit obtaining an observation image at the time of an examination for a medical treatment; a device information obtaining unit obtaining information of a device used at the time of the examination; an image setting information obtaining unit obtaining setting information associated with an observation image the same time the observation image is obtained by the image information obtaining unit; and a recording unit recording information composing of the image information obtained by the image information obtaining unit, the device information obtained by said device information obtaining unit and the image setting information obtained by the image setting information obtaining unit, as one associated information.

The invention recited in claim 5 records the image setting information (such as the degree of enhancement of an image, etc.) obtained by the image setting information obtaining unit, and the device information obtained by the device information obtaining unit by associating the image setting information and the device information with an observation image, the same time the observation image is recorded by the image information obtaining unit at the time of an examination, whereby a search or an inquiry is facilitated when the observation image is reproduced after the examination. Additionally, when the observation image is viewed after the examination, the information of the device used when the observation image is obtained, and information of a setting condition, etc. can be surely and easily extracted. Furthermore, based on image setting information (enhancement, contrast, etc.) or device information (such as the degree of brightness of a lamp in a light source device when an observation image is obtained), a change for removing a process executed for an observation image, or an image process for obtaining visual effects according to observer's likings can be performed with ease. As a result, more accurate diagnosis can be made.

An invention recited in claim 6 is a medical image recording system which comprises: a device information obtaining unit obtaining information of a device used for an examination for a medical treatment at the time of the examination; a message determining unit determining contents of a message based on the device information obtained by the device information obtaining unit; and a message displaying unit displaying the contents of the message determined by said message determining unit.

The invention recited in claim 6 achieves a good effect that contents of a message are determined by the message determining unit based on the device information obtained by the device information obtaining unit, and displayed, whereby the message according to the device can be displayed.

An invention recited in claim 7 is a medical image recording system which comprises: a device information obtaining unit obtaining information of a device used for an examination for a medical treatment at the time of the examination; a message determining unit determining contents of a message based on a type name of the device within the device information obtained by said device information obtaining unit; a display screen layout determining unit determining a display screen layout based on the type name of the device within the device information obtained by the device information obtaining unit; and a message displaying unit displaying the contents of the message determined by the message determining unit according to the screen display layout determined by said display screen layout determining unit.

The invention recited in claim 7 achieves a good effect that contents of a message are determined by the message determining unit based on the type name within the device information obtained by the device information obtaining unit, and the contents of the message are displayed, whereby the message in accordance with the device can be displayed.

Additionally, this invention also achieves a good effect that a display screen layout is determined by the display screen layout determining unit based on the type name within the device information obtained by the device information obtaining unit, whereby the message can be displayed in the display screen layout in accordance with the device.

An invention recited in claim 8 is the medical image recording system according to claim 3, wherein the data recorded by the drug or device information obtaining unit is reflected on an electronic carte.

The invention recited in claim 8 achieves a good effect that the data recorded by the drug information or the device information obtaining unit is automatically reflected on an electronic carte, whereby the drug or device information used at the time of the examination can be easily recorded on the electronic carte, a man-made input error is eliminated, and the data can be easily managed.

BRIEF DESCRIPTION OF THE DRAWINGS

The present invention will be more apparent from the following detailed description, when taken in conjunction with the accompanying drawings, in which:

FIG. 2 shows one example of a device data format;

FIG. 3 is a flowchart showing the outline of a process executed by a medical image recording system according to the first preferred embodiment;

FIG. 6 is a flowchart showing the outline of a process executed by a medical image recording system according to the third preferred embodiment;

FIG. 9 shows one example of an observation image of a high-definition endoscope;

FIG. 12 exemplifies the configuration of a circuit used in a preferred embodiment according to the present invention.

DESCRIPTION OF THE PREFERRED EMBODIMENTS

Hereinafter, preferred embodiments according to the present invention are described with reference to FIGS. 1 to 12.

Figure 1:
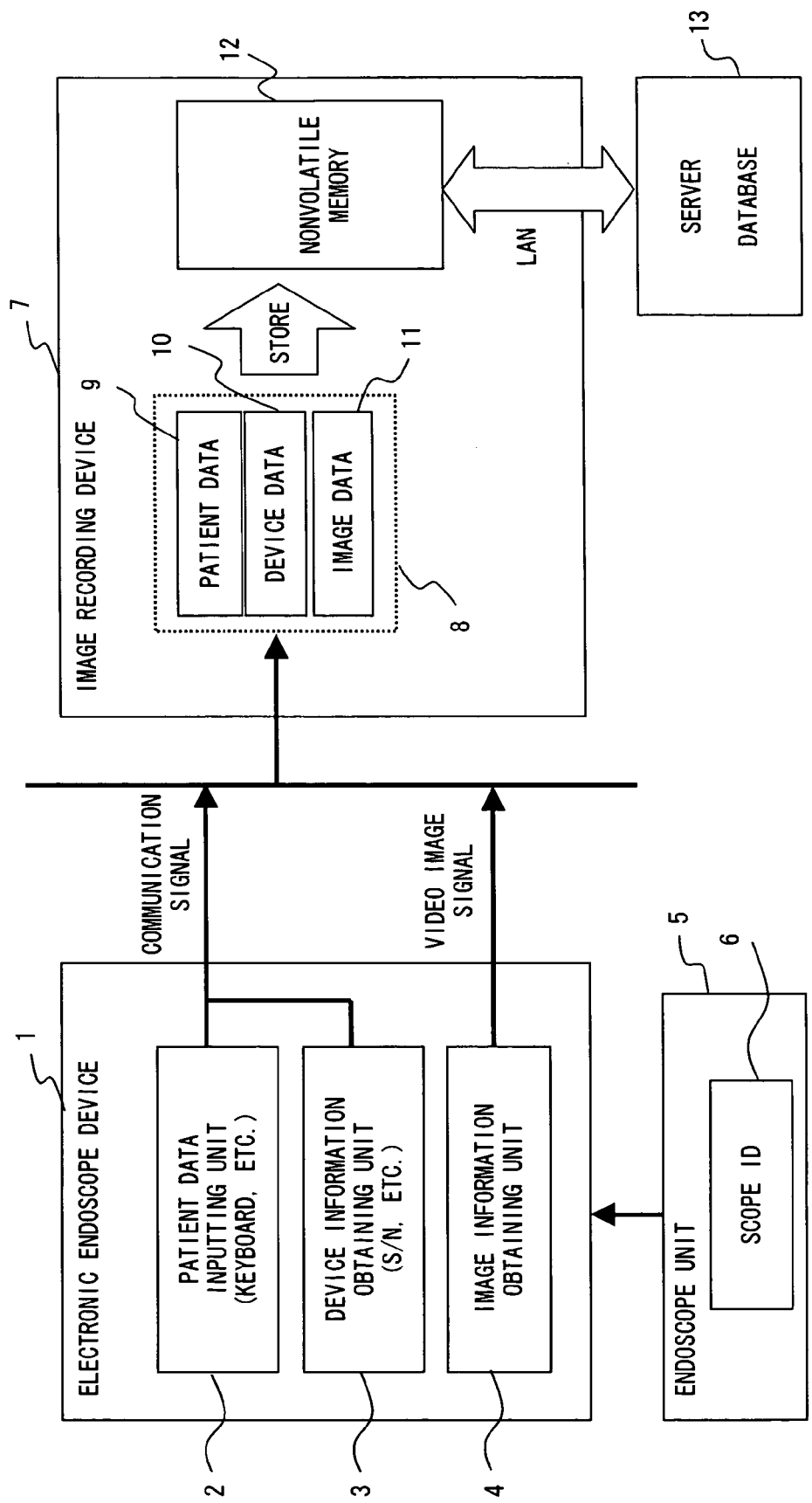
FIG. 1 is a block diagram showing the configuration of functions of a first preferred embodiment according to the present invention.

FIG. 1 shows the outline of the configuration of the first preferred embodiment according to the present invention.

An electronic endoscope device 1 comprises: a patient data inputting unit 2, for example, a keyboard, a mouse, etc., inputting patient data such as an ID number, an age, a sex, a name, etc. of a patient; a device information obtaining unit 3 obtaining device information such as a type name, an S/N, etc. of the electronic endoscope device 1, an endoscope unit 5 (including a scope ID 6 for identifying the endoscope unit 5) connected to the electronic endoscope device 1, a light source device (not shown) providing light to the endoscope unit 5; and a image information obtaining unit 4 processing a video image from the endoscope unit 5. The electronic endoscope device 1 further comprises: a light source device, not shown, emitting light for illuminating a sample via the endoscope unit 5; a image information obtaining unit 4, not shown, executing various signal processes by using, as a video image signal, an observation image of a sample, which is obtained by being illuminated by the light emitted from the light source device; and an observation monitor, not shown, displaying the video image signal.

Respective device information of the electronic endoscope device 1, the endoscope unit 5, the image recording device 7, and the light source device (not shown) are information such as a type name, an S/N, etc. as shown in FIG. 2, and stored, for example, in an EEPROM, etc., which is a nonvolatile memory within the respective devices. The electronic endoscope device 1 and the image recording device 7 are connected via a network. Communication signals of patient data, device information, a release instruction, etc., and video signals of image information, etc. can be transferred from the electronic endoscope device 1 to the image recording device 7. In the image recording device 7, the patient data 9 input from the patient data inputting unit 2, which is transmitted from the electronic endoscope device 1 via the network, the device data 10 obtained by the device information obtaining unit 3, and image data 11 are associated with one another and managed for each examination, and stored in the nonvolatile memory 12 as recorded data 8. Then, the recorded data 8 is transferred and stored in a server 13, in which a database is built, via a network. The image data 11 is generated by processing a video image, which is transmitted from the endoscope unit 5 to the electronic endoscope device 1, into a signal, which can be externally output, in the information obtaining unit 4, and by capturing the video image signal in a memory, which is provided within the image recording device 7 and not shown, when a user performs a release operation. An instruction of the release operation may be made from the electronic endoscope device 1 to the image recording device 7 as a communication signal via the network, or may be directly made to the image recording device 7.

Outline of the process executed in the first preferred embodiment according to the present invention is described with reference to a flowchart shown in FIG. 3.

When an examination is started, a patient data obtainment process in step S30 is executed. Namely, when patient data (an ID number unique to a patient, a name, a sex, etc. of the patient) is input from the patient data inputting unit, for example, a keyboard, a mouse, etc., which is connected to the electronic endoscope device 1, the data is transmitted from the electronic endoscope device 1 to the image recording device 7 via the network under the control of a CPU within the electronic endoscope device 1. The data transferred from the electronic endoscope device 1 is stored in a memory within the image recording device 7 as the patient data 9.

When the input of the patient data from the patient data inputting unit 2 of the electronic endoscope device 1 is completed in step S30, a process for obtaining information of a device, which is connected to the electronic endoscope device 1, is executed under the control of the CPU within the electronic endoscope device 1 in step S31. Under the control of the CPU, the electronic endoscope device 1 obtains information such as a type name, an S/N (serial number), a use time, the number of times of uses, etc. of the respective devices as shown in FIG. 2 by making data communications with the light source device (not shown), the endoscope unit 5, and the image recording device 7, which are connected to the electronic endoscope device 1. The obtained information is transferred from the electronic endoscope device 1 to the image recording device 7 via the network in a similar manner as in step S30, under the control of the CPU within the electronic endoscope device 1. The transferred data is recorded in the memory within the image recording device 7 as the device data 10.

When the obtainment of the device data 10 of the respective devices, which are connected to the electronic endoscope device 1, is completed, shooting with the endoscope is started in step S32. Namely, an examination is started, and made in such a way that shooting is made, for example, by inserting a body cavity inserting unit of the endoscope unit 5 in a body cavity, and the body cavity is observed with an observation monitor (not shown), which is connected to the electronic endoscope device 1 or the image recording device 7.

A user of the medical image recording system continues the examination while viewing the observation monitor, and executes a process for obtaining a video image (image data) of an affected part for a displayed image if necessary. Namely, a release operation for storing image information is performed by operating an operation unit of the endoscope unit 5. An instruction to capture the information of an image that a user requires among video images, which are transmitted from the endoscope unit 5 to the electronic endoscope device 1, is made to the image recording device 7 by performing the above described release operation under the control of the CPU within the electronic endoscope device 1, and the video image signal transmitted via the network is captured in the memory which is not shown and provided within the image recording device 7 as the image data 11. In step S34, it is determined whether or not the examination (shooting) is terminated. If the examination (shooting) is not terminated, the process in step S33 is repeated.

Upon termination of one examination (shooting), a data storage process in step S35 is executed. Namely, the image recording device 7 stores the patient data 9, the device data 10, and the image data 11, which are stored in the memory within the image recording device 7, in the nonvolatile memory 12 as the recorded data 8 of one examination. The recorded data 8 stored in the nonvolatile memory 12 is transmitted to the server 13, which renders a database service, via a LAN (Local Area Network).

This preferred embodiment refers to the configuration where images are collectively transmitted to the server 13 after an examination is terminated. However, for example, an image may be transmitted to the server 13 each time a release operation is performed, and an examination termination notification may be transmitted later.

Figure 4:
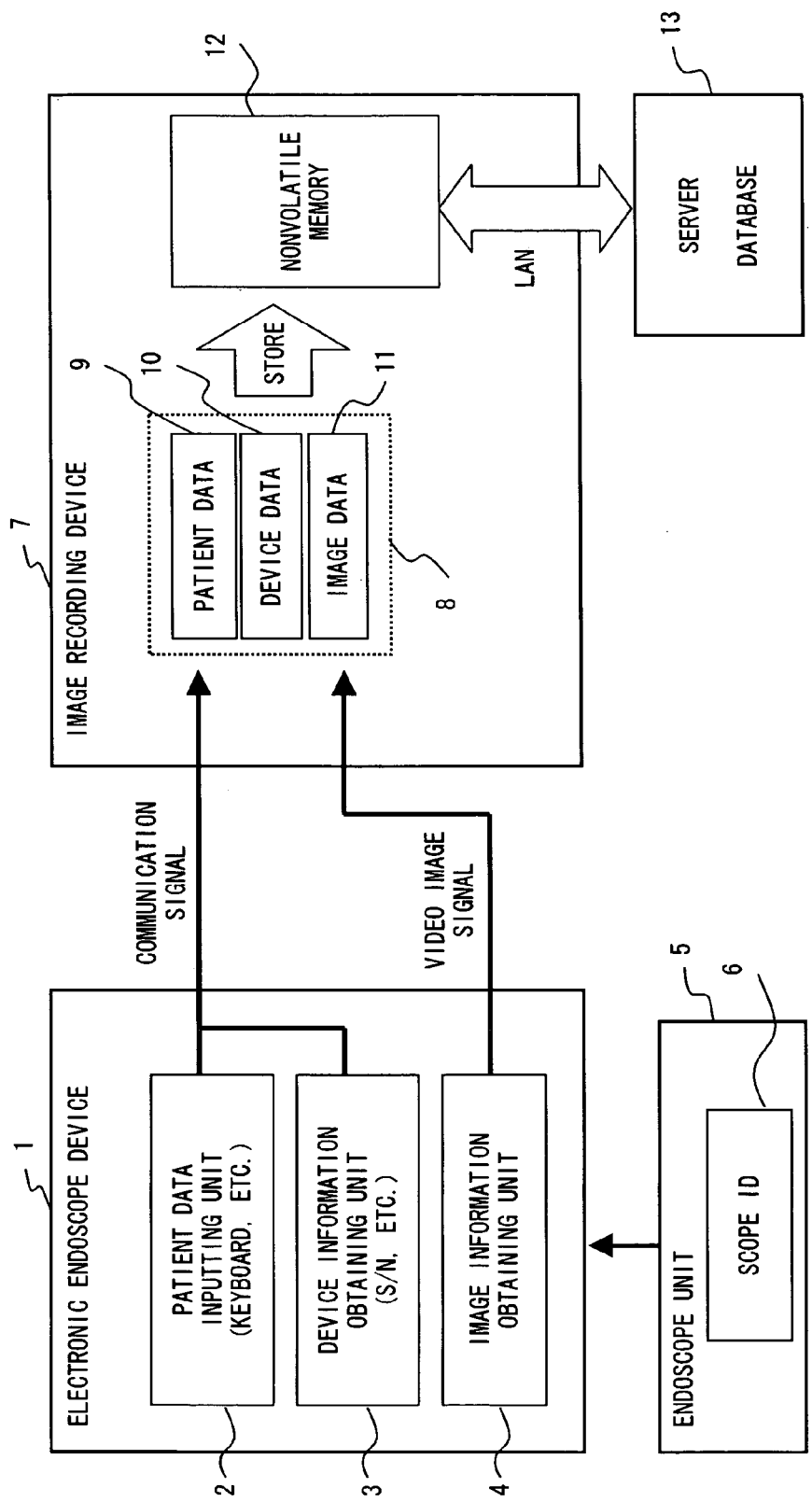
FIG. 4 shows the configuration of functions of a second preferred embodiment according to the present invention.

FIG. 4 shows the outline of the configuration of the second preferred embodiment according to the present invention.

Principal parts of the configuration of this preferred embodiment are similar to those of FIG. 1 except for a connection form of the electronic endoscope device 1 and the image recording device 7. An electronic endoscope device 1 comprises: a patient data inputting unit 2, for example, a keyboard, a mouse, etc., inputting patient data such as an ID number, an age, a sex, a name, etc. of a patient; a device information obtaining unit 3 obtaining device information such as a type name, an S/N, etc. of the electronic endoscope device 1, an endoscope unit 5 connected to the electronic endoscope device 1, and a light source device (not shown) providing light to the endoscope unit 5; and a image information obtaining unit 4 processing a video image from the endoscope unit 5. Respective device information of the electronic endoscope device 1, the endoscope unit 5, the image recording device 7, and the light source device (not shown) are information such as a type name, an S/N, etc. as shown in FIG. 2, and respectively stored, for example, in an EEPROM, etc., which is a nonvolatile memory within the respective devices. Between the electronic endoscope device 1 and the image recording device 7, for example, an RS232C cable for making a communication of patient data, device information, or a release instruction, and a video image transmission cable for transmitting image information are connected.

In the image recording device 7, patient data 9, which is transmitted from the electronic endoscope device 1 and input from the patient data inputting unit 2, device data 10 obtained by the device information obtaining unit 3, and image data 11 are associated with one another and managed for each examination, and stored in a nonvolatile memory 12 as recorded data 8. Then, the recorded data 8 is transferred and stored in a server 13, in which a database is built, via a network. The image data 11 is generated by processing a video image, which is transmitted from the endoscope unit 5 to the electronic endoscope device 1, into a video image signal, which can be externally output, in the image information obtaining unit 4, and by capturing the video image signal in a memory, which is provided within the image recording device 7 and not shown, when a user performs a release operation. An instruction of the release operation may be made from the electronic endoscope device 1 to the image recording device 7 as a communication signal, or may be made to the image recording device 7 directly.

Outline of the process executed in the second preferred embodiment according to the present invention is described with reference to the flowchart shown in FIG. 3.

When an examination is started, a patient data obtainment process in step S30 is executed. Namely, when patient data (an ID number unique to a patient, a name, a sex, etc. of the patient) is input from the patient data inputting unit, for example, a keyboard, a mouse, etc., which is connected to the electronic endoscope device 1, they are transmitted to the image recording device 7 via a communications cable (such as an RS232C, etc.) connected to the electronic endoscope device 1 and the image recording device 7 under the control of the CPU within the electronic endoscope device 1. The data transferred from the electronic endoscope device 1 is stored in the memory within the image recording device 7 as the patient data 9.

When the input of the patient data from the patient data inputting unit 2 of the electronic endoscope device 1 is completed in step S30, a process for obtaining information of a device, which is connected to the electronic endoscope device 1, is executed under the control of the CPU within the electronic endoscope device 1 in step S31. Under the control of the CPU, the electronic endoscope device 1 obtains information such as a type name, an S/N (serial number), a use time, the number of uses, etc. of the respective devices as shown in FIG. 2, by making data communications with the light source device (not shown), the endoscope unit 5, and the image recording device 7, which are connected to the electronic endoscope device 1. The obtained information is transferred to the image recording device 7 via the communications cable connected to the electronic endoscope device 1 and the image recording device 7 under the control of the CPU within the electronic endoscope device 1, in a similar manner as in step S30. The transferred data is recorded in the memory within the image recording device 7 as the device data 10.

When the obtainment of the device data 10 of the respective devices, which are connected to the electronic endoscope device 1, is completed, shooting with the endoscope is started in step S32. Namely, an examination is started, and made in such a way that shooting is made, for example, by inserting a body cavity inserting unit of the endoscope unit 5 into a body cavity, and the body cavity is observed with an observation monitor (not shown), which is connected to the electronic endoscope device 1 or the image recording device 7.

A user of the medical image recording system continues the examination while viewing the observation monitor, and executes a process for obtaining a video image (image data) of an affected part for a displayed image if necessary in step S33. Namely, a release operation for storing image information is performed by operating an operation unit of the endoscope unit 5. An instruction to capture information of an image that a user requires among video images, which are transmitted from the endoscope unit 5 to the electronic endoscope device 1, is made to the image recording device 7 by making a capturing instruction to the image recording device 7 by performing the above described release operation under the control of the CPU within the electronic endoscope device 1, and the video image signal transmitted from the video image signal cable at this time is captured in the memory, which is provided within the image recording device 7 and not shown, as the image data 11.

In step S34, it is determined whether or not the examination (shooting) is terminated. If the examination (shooting) is not terminated, the process in step S33 is repeated.

Upon termination of one examination (shooting), a data storage process in step S35 is executed. Namely, the image recording device 7 stores the patient data 9, the device data 10, and the image data 11, which are stored in the memory within the image recording device 7, in the nonvolatile memory 12 as the recorded data 8 of one examination. The recorded data 8 stored in the nonvolatile memory 12 is transmitted to a server 13, which renders a database service, via a LAN (Local Area Network).

This preferred embodiment refers to the configuration where images are collectively transmitted to the server 13 after the examination is terminated. However, for example, an image may be transmitted to the server 13 each time the release operation is performed, and an examination termination notification may be transmitted later.

Figure 5:
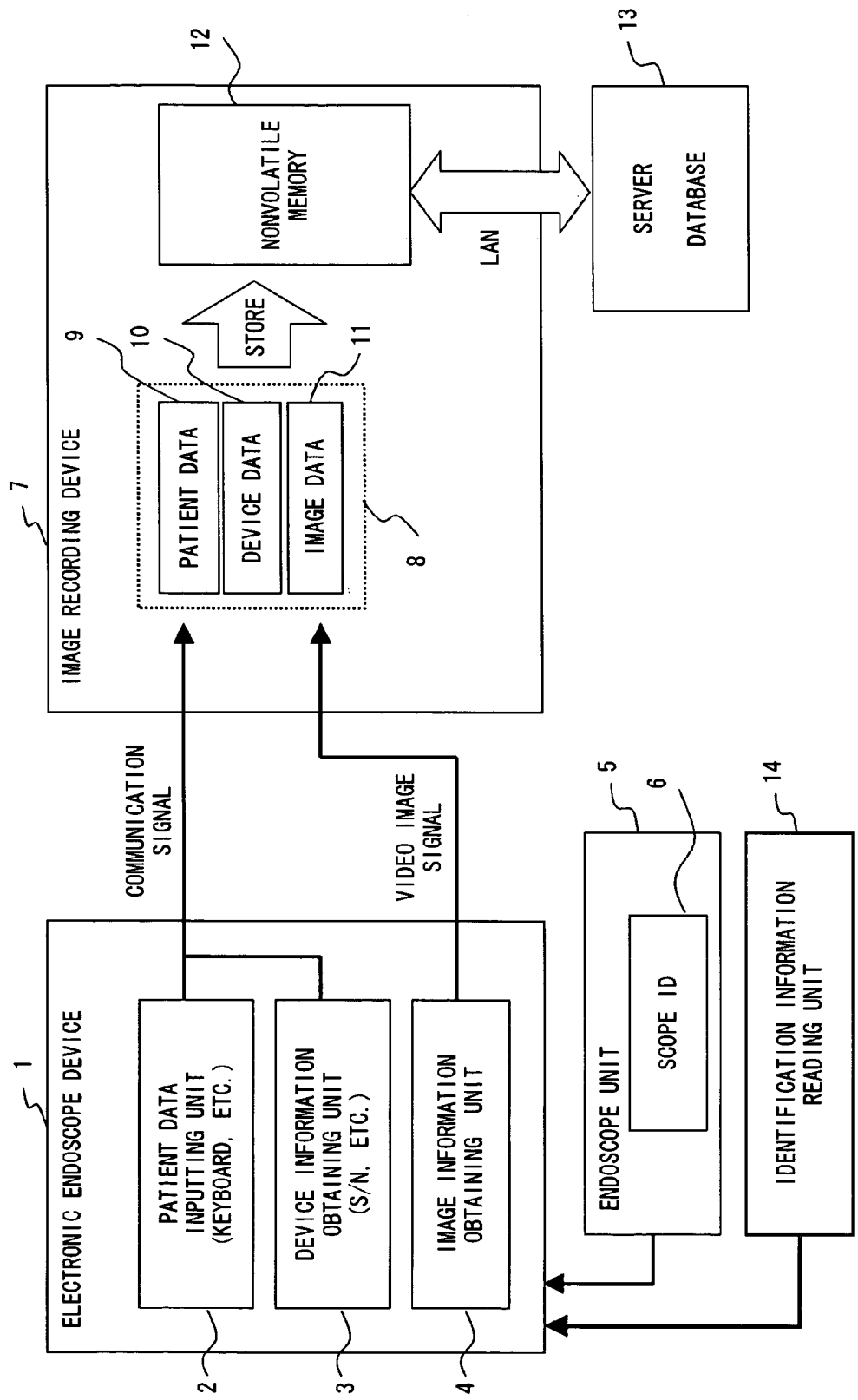
FIG. 5 shows the configuration of functions of a third preferred embodiment according to the present invention.

FIG. 5 shows the outline of the configuration of the third preferred embodiment according to the present invention. Configuration of an electronic endoscope device 1, an endoscope unit 5, and an image recording device 7 is similar to that described in the first preferred embodiment. The electronic endoscope device 1 comprises: a patient data inputting unit 2, for example, a keyboard or a mouse, inputting patient data such as an ID, an age, a sex, a name, etc. of a patient; a device information obtaining unit 3 obtaining device information such as a type name, an S/N, etc. of the electronic endoscope device 1, the endoscope unit 5, and a light source device (not shown), which are connected to the electronic endoscope apparatus 1; and a image information obtaining unit 4 processing a video image from the endoscope unit 5. Respective device information of the electronic endoscope device 1, the endoscope unit 5, the image recording device 7, and the light source device (not shown) are information such as a type name, an S/N, etc., as shown in FIG. 2, and respectively stored, for example, in an EEPROM, etc., which is a nonvolatile memory within the respective devices. Between the electronic endoscope device 1 and the image recording device 7, an RS232C cable for a communication of patient data, device information, or a release instruction, and a video image transmission cable for transmitting/receiving image information are connected. In the image recording device 7, the patient data 9, which is transmitted from the electronic endoscope device 1 and input from the patient data inputting unit 2, the device data 10 obtained by the device information obtaining unit 3, and the image data 11 are associated with one another and managed for each examination, and stored in a nonvolatile memory 12 as recorded data 8. Then, the recorded data 8 is transferred and stored in a server 13, in which a database is built, via a network. The image data 11 is generated by processing a video image, which is transmitted from the endoscope unit 5 to the electronic endoscope device 1, into a video image signal, which can be externally output, in the image information obtaining unit 4, and by capturing the video image signal in a memory, which is provided within the image recording device 7 and not shown, when a user performs a release operation. An instruction of the release operation may be made from the electronic endoscope device 1 to the image recording device 7 as a communication signal, or may be directly made to the image recording device 7.

In the configuration of the third preferred embodiment, an identification information reading unit 14 is connected to the electronic endoscope device 1 in addition to the configuration similar to the above described first preferred embodiment. With the identification information reading unit 14, an identification information storing unit, which is written in a drug and a device used for an examination at the time of the examination, or in a device that is used for the examination and not connected to the electronic endoscope device 1, is read, whereby the information of the drug and the device used for the examination, and the information of the device that is used for the examination and not connected to the electronic endoscope device 1 can be obtained.

Here, the identification information storing unit is, for example, an RF-ID (Radio Frequency IDentification), etc., which records unique information, and the identification information reading unit 14 contacts or non-contacts the identification information storing unit to read stored information.

Outline of the process executed in the third preferred embodiment according to the present invention is described with reference to a flowchart shown in FIG. 6.

Similar to the outline of the process executed in the first preferred embodiment, a patient data obtainment process in step S50 is first executed when an examination is started. Namely, when patient data (an ID number unique to a patient, a name, a sex, etc. of the patient) is input from the patient data inputting unit, for example, a keyboard, a mouse, etc., which is connected to the electronic endoscope device 1, the data is transmitted to the image recording device 7 via a communications cable under the control of a CPU within the electronic endoscope device 1, and stored in the memory within the image recording device 7 as the patient data 9.

When the input of the patient data from the patient data inputting unit 2 of the electronic endoscope device 1 is completed, a process for obtaining device information is executed in step S51. Namely, the process for obtaining the information of a device, which is connected to the electronic endoscope device 1, is executed under the control of the CPU within the electronic endoscope device 1. Under the control of the CPU, the electronic endoscope device 1 obtains the information such as a type name, an S/N (serial number), a use time, the number of times of uses, etc. of the respective devices as shown in FIG. 2, by making data communications with the light source device (not shown), the endoscope unit 5, and the image recording device 7, which are connected to the electronic endoscope device 1. The obtained information is transferred to the image recording device 7 via the communications cable under the control of the CPU within the electronic endoscope device 1 in a similar manner as in step S50. The transferred data is recorded in the memory within the image recording device 7 as the device data 10. Also information of a device which is used at the time of the examination and not connected to the electronic endoscope device 1 is obtained by reading the identification information storing unit written in the device with the identification information reading unit 14 connected to the electronic endoscope device 1. The obtained information is transmitted to the image recording device 7 via a data communications cable, and stored in the memory within the image recording device 7 as the device data 10.

Furthermore, a process for obtaining drug information is executed in step S52. Namely, also the information of a drug used at the time of the examination is obtained from the identification information storing unit written in the drug by using the identification information reading unit 14. The obtained information is transferred to the image recording device 7 via the communications cable under the control of the CPU within the electronic endoscope device 1, and recorded in the memory within the image recording device 7 as the device data 10.

Here, also the device information obtained by the device information obtaining unit 3 may be obtained from the identification information storing unit written in a device by using the identification information reading unit 14. With the identification information reading unit 14 connected to the electronic endoscope device 1, information of a device used for an examination can be obtained at the time of the examination with ease, and without causing a man-made error such as input error.

After the obtainment of the device data 10 of the respective devices, which are connected to the electronic endoscope device 1, is completed, an examination (shooting) with the endoscope is started in step S53, and made in such a way that shooting is made, for example, by inserting a body cavity inserting unit of the endoscope unit 5 in a body cavity, and the body cavity is observed with an observation monitor (not shown), which is connected to the electronic endoscope device 1 or the image recording device 7.

A user of the medical image recording system continues the examination while viewing the observation monitor, and executes a process for obtaining a video image (image data) of an affected part for a displayed image if necessary in step S54. Namely, a release operation for storing image information is performed by operating an operation unit of the endoscope unit 5.

An instruction to capture information of an image desired to be captured among video images transmitted from the endoscope unit 5 to the electronic endoscope device 1 is made to the image recording device 7 by operating the operation unit of the endoscope unit 5 under the control of the CPU within the electronic endoscope device 1, and the video image signal transmitted from the video image transmission cable at this time is captured in the memory which is provided within the image recording device 7 and not shown as the image data 11.

In step S55, it is determined whether or not the shooting is terminated. If the (examination) shooting is terminated, a data storage process in step S56 is executed. Namely, the image recording device 7 stores the patient data 9, the device data 10, and the image data 11, which are stored in the memory within the image recording device 7, in the nonvolatile memory 12 as the recorded data 8 of one examination. The recorded data 8 stored in the nonvolatile memory 12 is transmitted to the server, which renders a database service, via a LAN (Local Area Network).

This preferred embodiment refers to the configuration where the device information obtainment process S51 and the drug information obtainment process S52 are executed before shooting is started. However, the preferred embodiment is not limited to this implementation. Since a drug is sometimes added after shooting is started, steps S51 and S52 may be executed on demand before data is stored in step S56.

Figure 7:
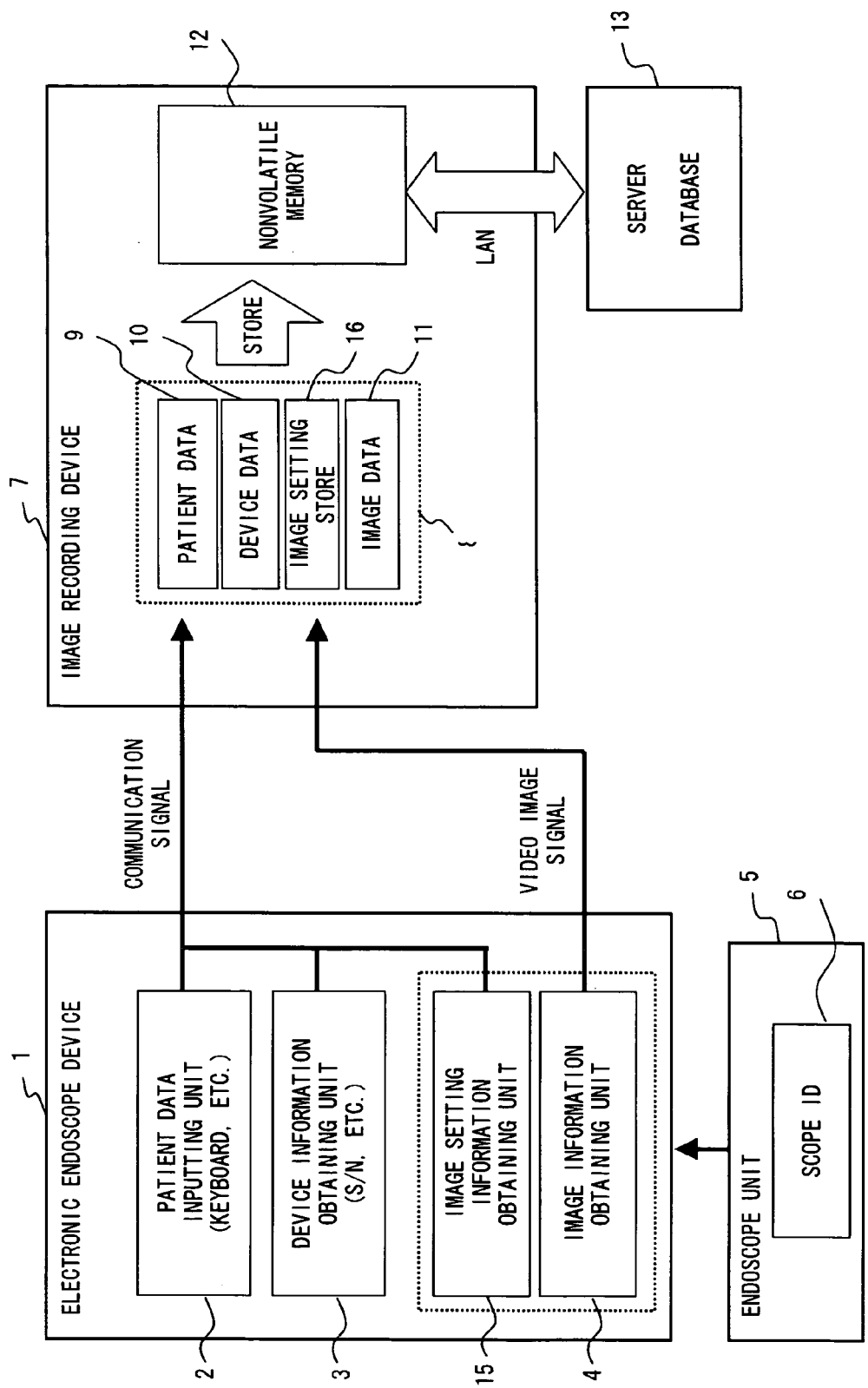
FIG. 7 shows the configuration of functions of a fourth preferred embodiment according to the present invention.

FIG. 7 shows the outline of the configuration of the fourth preferred embodiment according to the present invention. Similar to the first preferred embodiment, an electronic endoscope device 1 comprises: a patient data inputting unit 2, for example, a keyboard or a mouse, inputting patient data; a device information obtaining unit 3 obtaining device information such as a type name, an S/N of the electronic endoscope device 1, an endoscope unit 5 and a light source device (not shown), which are connected to the electronic endoscope device 1; and a image information obtaining unit 4 processing a video image from the endoscope unit 5. The electronic endoscope device 1 further comprises an image setting information obtaining unit 15 obtaining information of an image process executed for captured image information when a video image transmitted from the endoscope unit 5, which is connected to the electronic endoscope device 1, to the electronic endoscope device 1 is captured under the control of the CPU.

Between the electronic endoscope device 1 and the image recording device 7, for example, an RS232C cable for making a communication of patient data, device information, image information, or a release instruction, and a video image transmission cable for transmitting/receiving image information are connected. In the image recording device 7, patient data 9, which is transmitted from the electronic endoscope device 1 and input from the patient data inputting unit 2, device data 10, which is obtained by the device information obtaining unit 3, image data 11 obtained by capturing a video image, which is transmitted from the endoscope unit 5 to the electronic endoscope device 1, by the image information obtaining unit 4, and image settings 16 when the image information is obtained are associated with one another and managed for each examination, and stored in a nonvolatile memory 12.

Then, the recorded data is transferred and stored in a server 13, in which a database is built, via a network.

Outline of the process executed in the fourth preferred embodiment according to the present invention is described with reference to the flowchart shown in FIG. 3.

When an examination is started, a patient data obtainment process in step S30 is executed. Namely, when patient data is input from the patient data inputting unit, for example, a keyboard, amuse, etc., which is connected to the electronic endoscope device 1, the data is transmitted to the image recording device 7 via a communications cable connected to the electronic endoscope device 1 and the image recording device 7 under the control of the CPU within the electronic endoscope device 1. The transferred data is stored in the memory within the image recording device 7 as the patient data 9.

When the input of the patient data 9 is completed in step S30, a process for obtaining information of a device, which is connected to the electronic endoscope device 1, is executed under the control of the CPU within the electronic endoscope device 1 in step S31. under the control of the CPU, the electronic endoscope device 1 obtains information such as a type name, an S/N (serial number), a use time, the number of uses, etc. of the respective devices as shown in FIG. 2, by making data communications with the light source device (not shown), the endoscope unit 5, and the image recording device 7, which are connected to the electronic endoscope device 1, and. The obtained information is transferred to the image recording device 7 via a communications cable connected to the electronic endoscope device 1 and the image recording device 7 under the control of the CPU within the electronic endoscope device 1 in a similar manner as in step S30, and the information is recorded in a memory within the image recording device 7 as the device data 10.

When the obtainment of the device data 10 of the respective devices, which are connected to the electronic endoscope device 1, is completed, shooting with the endoscope in step S32 is started. Namely, an examination is started, and made in such a way that shooting is made, for example, by inserting a body cavity inserting unit of the endoscope unit 5 in a body cavity, and the body cavity is observed with an observation monitor (not shown), which is connected to the electronic endoscope device 1 or the image recording device 7.

A user of the medical image recording system continues the examination while viewing the observation monitor, and executes a process for obtaining a video image (image data) of an affected part in step 33 for a displayed image if necessary. Namely, a release operation for storing image information is performed by operating an operation unit of the endoscope unit 5. An instruction to capture the information of an image that a user requires among video images, which are transmitted from the endoscope unit 5 to the electronic endoscope device 1, is made to the image recording device 7 by performing the above described release operation under the control of the CPU within the electronic endoscope device 1, and the video image signal transmitted from the video image transmission cable at this time is captured in the memory which is provided within the image recording device 7 and not shown as the image data 11.

In the fourth preferred embodiment, a setting condition of an image process when shooting is made (when image information is obtained) is obtained as image setting information the same time the image information is captured. The CPU within the electronic endoscope device 1 obtains the image setting information of the image process simultaneously with the capturing process of the image, and transmits the obtained information to the image recording device 7 via the communications cable. The image setting information transmitted from the electronic endoscope device 1 is stored in the memory within the image recording device 7 as image settings 16.

In step S34, it is determined whether or not the examination (shooting) is terminated. If the examination (shooting) is not terminated, the process in step S33 is repeated.

Upon termination of one examination (shooting), a data storage process in step S35 is executed. Namely, the image recording device 7 stores the patient data 9, the device data 10, the image data 11, and the image settings 16, which are stored in the memory within the image recording device 7, in the nonvolatile memory 12 as the recorded data 8 of one examination. The recorded data 8 stored in the nonvolatile memory 12 is transmitted to the server 13, which renders a database service, via a LAN (Local Area Network).

In the conventional image recording systems, a 1-to-1 association exists between an image recording device 7 and a device connected to the image recording device 7, for example, between the image recording device 7 and the electronic endoscope device 1. Since a device connected to the image recording device 7 is identified as described above, an error message can be displayed according to a predetermined screen display layout, and can be displayed in a position where a video image shot at the time of an examination is not hidden, when the error message can be displayed on a display screen such as an observation monitor, etc.

However, if a plurality of devices such as an ultrasound device, etc. are connected to the image recording device 7 (if an association between the image recording device 7 and devices connected to the image recording device 7 is 1 to n), there arises a problem that an image shot at the time of an examination is hidden by a displayed message if the error message is displayed in a predetermined screen position according to a predetermined display screen layout as in the conventional systems, and a problem that only a uniform message can be displayed although contents of an error or contents of a measure against an error vary by medical device, and it is difficult for a user to understand how to cope with an error.

Figure 8:
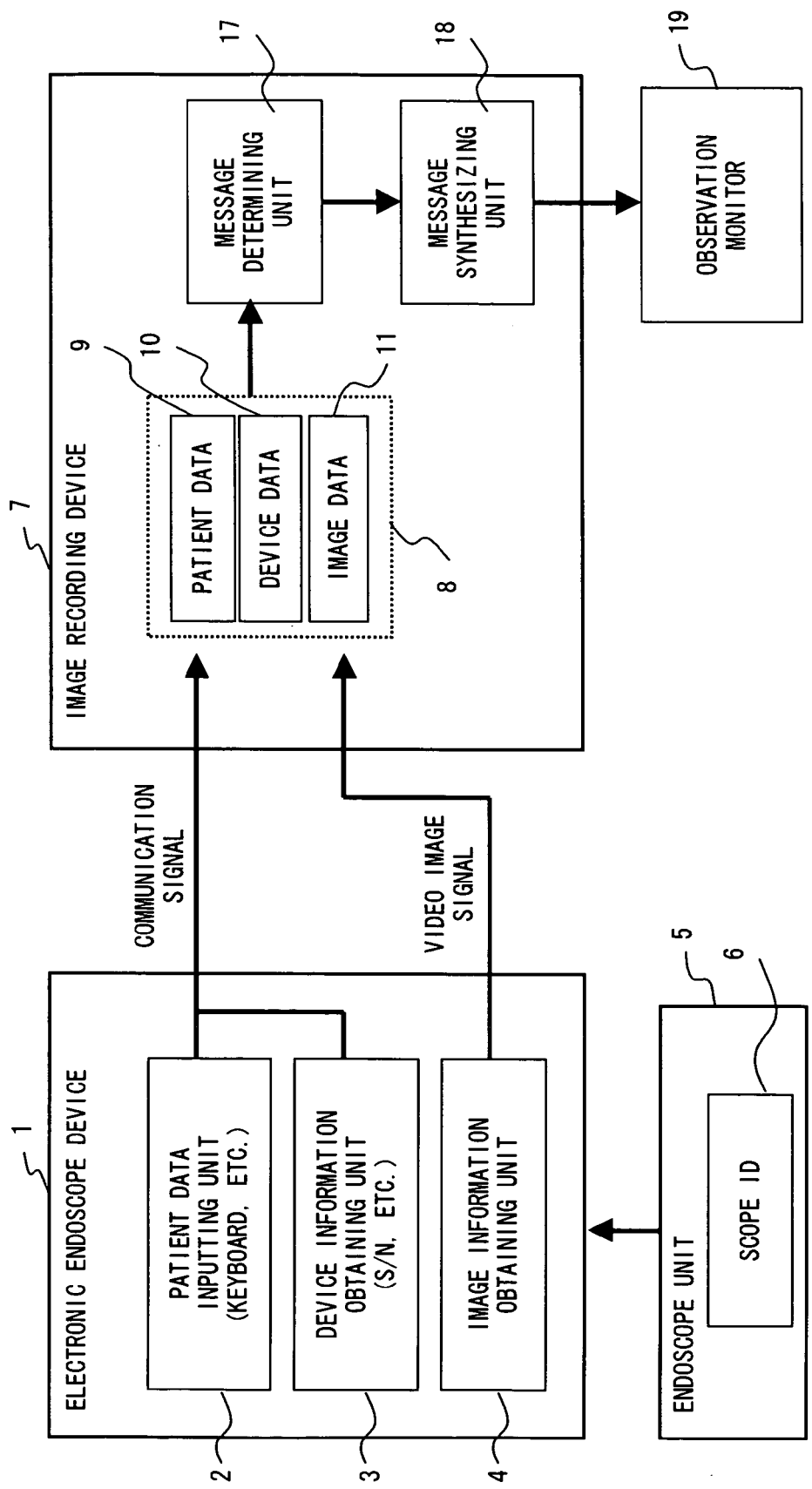
FIG. 8 shows the configuration of functions of a fifth preferred embodiment according to the present invention.

The above described problems can be solved by determining a position in which a message is displayed (display layout) and contents of the message based on the device data 10, which is obtained by the device information obtaining unit 3, and by displaying the message on the observation monitor as shown in FIG. 8.

In FIG. 8, in a similar manner as in the first preferred embodiment, when patient data is input from a patient data inputting unit, for example, a keyboard, a mouse, etc., which is connected to the electronic endoscope device 1, the patient data is transmitted to an image recording device 7 via a communications cable connected to the electronic endoscope device 1 and the image recording device 7 under the control of a CPU within the electronic endoscope device 1, and stored in the memory within the image recording device 7 as patient data 9. When the input of the patient data 9 is completed, a process for obtaining information of a device, which is connected to the electronic endoscope device 1, is executed under the control of the CPU within the electronic endoscope device 1. Furthermore, data communications are made with a light source device (not shown), an endoscope unit 5, and the image recording device 7, which are connected to the electronic endoscope device 1, and device information of the respective devices are obtained under the control of the CPU within the electronic endoscope device 1 in a similar manner as in the first preferred embodiment. The obtained information is transferred to the image recording device 7 via the communications cable connected to the electronic endoscope device 1 and the image recording device 7, and recorded to a memory within the image recording device 7 as device data 10, under the control of the CPU within the electronic endoscope device 1.

Figure 10:
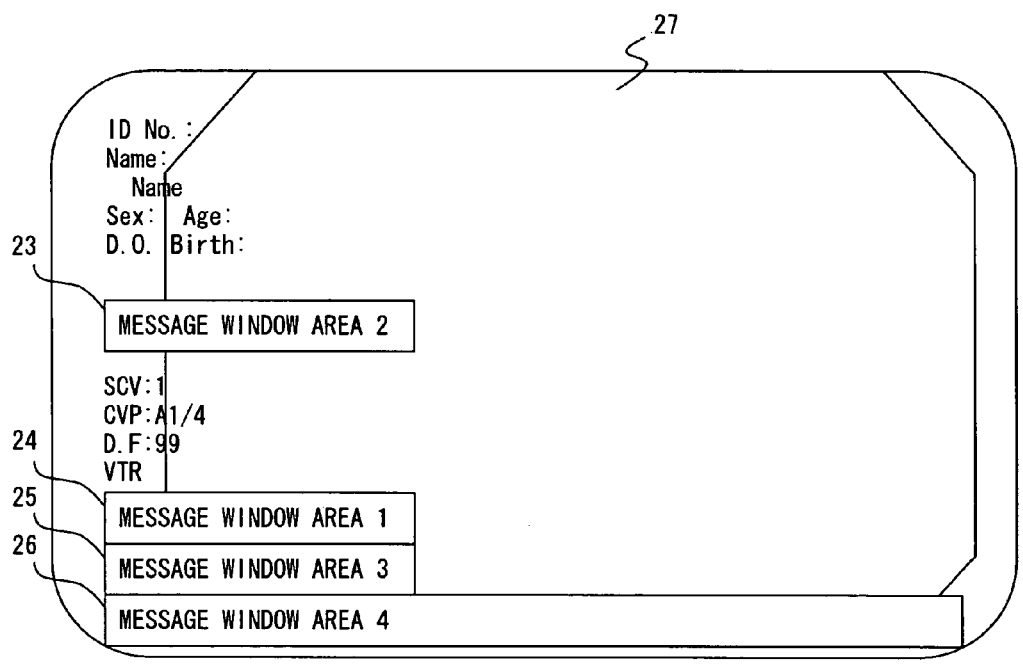
FIG. 10 shows one example of an observation image of a standard endoscope.
Figure 11:
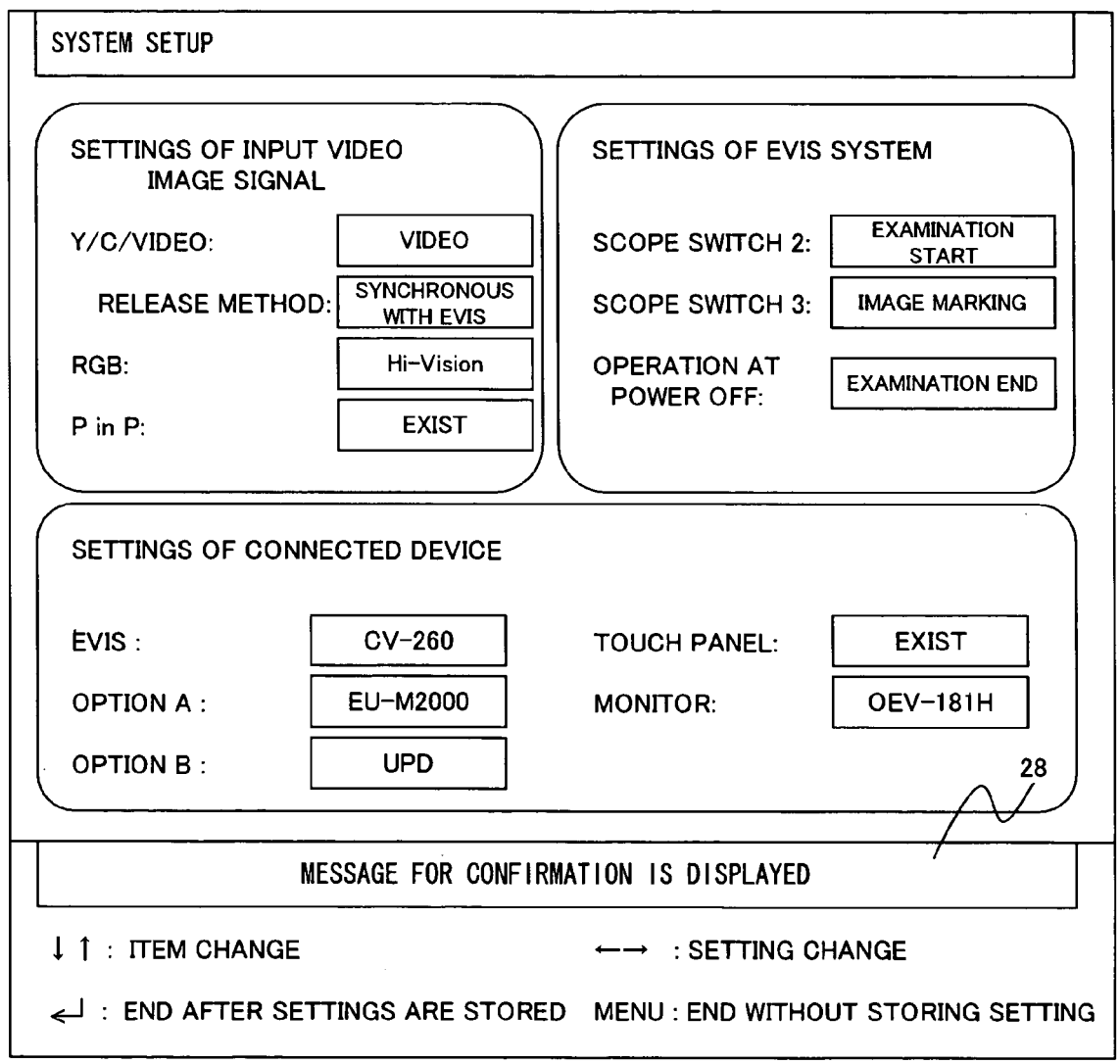
FIG. 11 shows one example of a message display screen.

Here, to display an error message, the message to be displayed on the screen of the observation monitor 19 is created and a layout of the display screen is determined by a message determining unit 17 based on the device data 10 obtained by the device information obtaining unit 3. For example, device data stored in the memory is referenced, and whether the observation monitor 19 is either high-definition or standard is determined under the control of the CPU within the image recording device 7. FIG. 9 shows one example of the screen of the observation monitor of the high-definition endoscope. This screen has message window areas 20 and 21, which are areas for displaying a message of an error, etc. An observation image is displayed in an observation image displaying part 22. FIG. 10 shows one example of the screen of the observation monitor of the standard endoscope. This screen has four message window areas 23 to 26 as areas for displaying a message of an error, etc. An observation image is displayed in an observation image displaying part 27. If the observation monitor 19 is a monitor of the high-definition endoscope, the screen shown in FIG. 9 is determined as the display screen layout. Or, if the observation monitor 19 is a monitor of the standard endoscope, the screen shown in FIG. 10 is determined as the display screen layout. Or, for example, a product generation of the endoscope unit 5, etc. are automatically determined based on the device data obtained by the device information obtaining unit 3 under the control of the CPU, and a display screen layout which fits each product generation is determined. After the layout of the display screen is determined, a message pattern that fits the layout is generated under the control of the CPU. The generated message is incorporated in a shot image by a message synthesizing unit 18, and displayed on the observation monitor 19.

For operations such as settings, etc. of a conventional device, an error message is displayed after a series of setting operations are performed. Accordingly, there is a problem that an operation to be performed next is difficult to be determined from a displayed error message, and a problem that a detailed error message is needless for a user who is familiar with the device, but a user who is unfamiliar with the device does not know how to cope with a simple error message. In the message determining unit 17 shown in FIG. 8, a message instructing which setting operation to be performed next can be created and displayed on a screen if one item is set at the time of normal setting operations, a message instructing how to cope with a detected error can be displayed (in a message displaying part 28 shown in FIG. 11) if the error is detected at the time of setting operations, or a message which suits the device familiarity of a user can be created and displayed on the screen by presetting the degree of the device familiarity.

FIG. 12 shows the configuration of a circuit used in a preferred embodiment according to the present invention.

In an electronic endoscope device 1, a CPU 29, a memory 30 (a ROM, an EEPROM, etc. as a nonvolatile memory, a RAM, etc. as a volatile memory), an input device 31 (a keyboard, a mouse, etc.), an output device 32 (an observation monitor, an IF for an image signal, an I/F for an electric communication, or the like), an external storage device 33 (a hard disk, an optical disk device, etc.), a medium driving device 34 (a CDROM drive device), a network connecting device 36, and an image processing unit (not shown) are provided, and interconnected by a bus 38.

The CPU 29 reads a program for controlling the electronic endoscope device 1 from, for example, the ROM as the nonvolatile memory, or from the hard disk as the external storage device 33, and performs a control according to the program. The CPU 29 also executes a process for writing/reading data to/from the RAM. For example, in an EEPROM as the nonvolatile memory, device information such as a type name, an S/N, etc. is stored as exemplified in FIG. 2. The CPU 29 reads the device information from the EEPROM, and temporarily writes the information to the RAM on demand. After the device information of all of devices, which are connected to the electronic endoscope device 1, is read out, the information is transmitted to the image recording device 7 via a communications cable (such as RS232C).

After image information transmitted from the endoscope unit 5 is temporarily stored in the volatile memory such as a RAM, etc. via the I/F for an image signal, it is transmitted to the image processing unit (not shown), which then processes the image information according to the settings of an operator. For the processed image information, processes such as D/A conversion, etc. are executed, and, for example, a resultant RGB video image signal is output to the observation monitor as the output device 32, and displayed on the observation monitor.

In the endoscope unit 5, a CPU 29, a memory 30 (a ROM, an EEPROM, etc. as a nonvolatile memory, or a RAM, etc. as a volatile memory), an input device 31 (an operation unit or a body cavity inserting unit, etc. of the endoscope unit 5), and an output device 32 (an I/F for an image signal, an I/F for an electric communication, or the like) are provided, and interconnected by a bus 38.

The CPU 29 reads a program for controlling the endoscope unit 5 from, for example, the ROM or the EEPROM as the nonvolatile memory, and performs a control according to the program. The CPU 29 also executes a process for writing/reading data to/from the RAM. For example, in the EEPROM as the nonvolatile memory, device information such as a type name, an S/N, the number of uses, etc. is stored as exemplified in FIG. 2. If an instruction to read the device information is made from the electronic endoscope device 1 via the I/F for an electric communication, the device information is read from the EEPROM under the control of the CPU 29, and transmitted to the electronic endoscope device 1 via the I/F for an electric communication.

In the image recording device 7, a CPU 29, a memory 30 (a ROM, an EEPROM, etc. as a nonvolatile memory, or a RAM, etc. as a volatile memory), an input device 31 (a keyboard, a mouse, etc.), an output device 32 (an observation monitor, an I/F for an image signal, an IF for an electric communication, or the like), an external storage device 33 (a hard disk, an optical disk device, etc.), a medium driving device 34 (such as a CDROM drive device) for reading/writing data to a portable storage medium 35, and a network connecting device 36 are provided, and interconnected by a bus 38.

The CPU 29 reads a program for controlling the image recording device 7, for example, from the ROM as the nonvolatile memory, or from the hard disk as the external storage device 33, and performs a control according to the program. The CPU 29 also executes a process for writing/reading data to/from the RAM. For example, in the EEPROM as the nonvolatile memory, device information such as a type name, an S/N, etc. is stored as exemplified in FIG. 2. If an instruction to read the device information is made from the electronic endoscope device 1 via the I/F for an electric communication, the device information is read from the EEPROM under the control of the CPU 29, and transmitted to the electronic endoscope device 1 via the I/F for an electric communication.

After image information transmitted from the electronic endoscope device 1 is temporarily stored in the volatile memory such as a RAM, etc. via the I/F for an image signal, it is stored, for example, in the EEPROM as the nonvolatile memory. Or, the image information is stored in the EEPROM, etc. directly via the I/F for an image signal. Similarly, patient data and device data, which are transmitted from the electronic endoscope device 1 via the I/F for an electric communication, are stored in the EEPROM, etc. after being temporarily stored in the volatile memory such as the RAM, etc., or stored directly from the electronic endoscope device 1 via the I/F for an electric communication. The data stored in the EEPROM, etc. is stored on a hard disk etc. as the external storage device 33 within the image recording device 7, or transmitted and stored in a server, which renders a database service, via the network connecting device 36 and the network 37.

Note that the nonvolatile memory is not limited to the EEPROM. A flash memory, etc. may be available.

In the descriptions of the first, the third, and the fourth preferred embodiments, the recorded data 8 for which an association is made for each examination is not limited to be recorded to a server on a network via a LAN. The recorded data 8 may be recorded to an external storage device such as a hard disk (magnetic disk), etc., which is directly connected to the image recording device 7.

Additionally, the recorded data 8 is not limited to being stored in the external storage device, and may be stored within the image recording device 7 by using a nonvolatile memory such as a flash memory, etc.

Furthermore, the process for making an association for each examination may be executed by the image recording device 7, and may be executed with a database function.

The order of the patient data obtainment process, which is executed by the patient data inputting unit 2, the device information obtainment process, which is executed by the device information obtaining unit 3, and the image information obtainment process, which is executed by the image information obtaining unit 4, is not limited to the order shown in FIG. 3. For example, the patient data obtainment process and the device information obtainment process may be executed after image information is obtained by the image information obtaining unit 4, when one examination is made. Similarly, also the order of the patient data obtainment process, which is executed by the patient data inputting unit 2, the device information obtainment process, which is executed by the device information obtaining unit 3, the image information obtainment process, which is executed by the image information obtaining unit 4, and the drug information obtainment process, which is obtained by the identification information reading unit 14, or the process for obtaining information of a device, which is not connected to the electronic endoscope device 1, is not limited to the order shown in FIG. 6. Here, data recorded as a result of the drug information obtainment process and the device information obtainment process may be reflected, for example, on an electronic carte created after an examination is terminated.

When one examination is continued, the patient data 9 obtained by the patient data inputting unit 2, the device data 10 obtained by the device information obtaining unit 3, and the image data 11 obtained by the image information obtaining unit 4 do not always need to be temporarily stored in the memory within the image recording device 7, and may be directly stored, for example, in an EEPROM, etc. as a nonvolatile memory within the image recording device 7.

As described above, according to the present invention recited in claims 1 and 2, the image information, which is obtained by the image information obtaining unit at the time of an examination, and the device information, which is obtained by the device information obtaining unit and used at the time of the examination, are recorded as one associated information by the recording unit, whereby a search or an inquiry of the device information used at the time of the examination can be easily made when the image information is reproduced after the examination. Additionally, when contents of an examination made are recorded with an electronic carte, etc., information of a device used for an examination is automatically recorded simultaneously with the examination without relying on a hand-written note, memory, etc. when contents of an examination made are recorded with an electronic carte, etc., whereby the amount of input operations can be significantly reduced, and a recording error of device information, which is resultant from a man-made input error, etc., can be eliminated.

Additionally, according to the present invention recited in claims 3 and 4, the image information, which is obtained by the image information obtaining unit at the time of an examination, and the information of a drug or a device used at the time of the examination, which is obtained by the drug or device information obtaining unit, are recorded as one associated information by the recording unit, whereby a search or an inquiry of the information of the device used at the time of the examination can be facilitated when image information is reproduced after the examination. Additionally, when contents of an examination made are recorded with an electronic carte, information of a device and a drug, which are used for the examination, can be recorded simultaneously with the examination without relying on a hand-written note, memory, etc. As a result, input operations can be significantly reduced, and at the same time, a recording error of device information and drug information, which is resultant from a man-made error such as an input error, can be prevented from occurring.

What is claimed is:

1. A medical image recording system, comprising:
   an image information obtaining unit for obtaining an observation image at the time of an examination for a medical treatment;
   a device information obtaining unit for obtaining information of the image information obtaining unit and information of devices including at least one image capture device connected to the image information obtaining unit and at least one non-connected external device in active use in combination with the image capture device in use at the time of the examination, the device information obtained by said device information obtaining unit includes at least one of a type name, a serial number, a use time, a number of uses, and a setting value of the devices used at the time of the examination; and
   a recording unit for recording information including the image information obtained by said image information obtaining unit and the device information obtained by said device information obtaining unit, as a single examination record.

2. A medical image recording system, comprising:
   an image information obtaining unit for obtaining an observation image at the time of an examination for a medical treatment;
   a device information obtaining unit for obtaining information of the image information obtaining unit and information about a device being used while the device is connected to the image information obtaining unit;
   an identification information obtaining unit for obtaining identification information about a non-connected examination device being used during the examination without being connected to the medical image recording system and while the non-connected examination device is in active use, and/or identification information about a drug used at the time of the examination; and
   a recording unit for recording the image information obtained by said image information obtaining unit, the information about the device obtained by the device information obtaining unit, and the information obtained by the identification information obtaining unit, as a single examination record.

3. The medical image recording system according to claim 2, wherein said identification information obtaining unit is an identification information reading unit reading identification information written in the drug or the device, which is used at the time of the examination.

4. A medical image recording system, comprising:
   an image information obtaining unit obtaining an observation image at the time of an examination for a medical treatment;
   a device information obtaining unit for obtaining information of the image information obtaining unit and information of devices including at least one image capture device connected to the image information obtaining unit and at least one non-connected external device in active use in combination with the image capture device in use at the time of the examination, the device information obtained by said device information obtaining unit includes at least one of a type name, a serial number, a use time, a number of uses, and a setting value of the devices used at the time of the examination;
   an image setting information obtaining unit obtaining setting information associated with an observation image the same time the observation image is obtained by said image information obtaining unit; and
   a recording unit recording information composing of the image information obtained by said image information obtaining unit, the device information obtained by said device information obtaining unit and the image setting information obtained by said image setting information obtaining unit, as a single examination record.

5. A medical image recording system, comprising:
   a device information obtaining unit obtaining information of an image capture device and a non-connected external device used in combination with the image capture device used for an examination for a medical treatment at the time of the examination, the device information obtained by said device information obtaining unit includes at least one of a type name, a serial number, a use time, a number of uses, and a setting value of the devices used at the time of the examination;
   a message determining unit determining contents of a message based on a type name within the device information obtained by said device information obtaining unit;
   a display screen layout determining unit determining a display screen layout based on the type name of the device within the device information obtained by said device information obtaining unit; and
   a message displaying unit displaying the contents of the message determined by said message determining unit according to the screen display layout determined by said display screen layout determining unit.

6. The medical image recording system according to claim 2, wherein the data recorded by said drug or device information obtaining unit is reflected on an electronic carte.

7. A medical image recording system, comprising:

image information obtaining means for obtaining an observation image at the time of an examination for a medical treatment;

device information obtaining means for obtaining information of the image information obtaining means and information of devices including at least one image capture device connected to the image information obtaining unit and at least one non-connected external device in active use in combination with the image capture device in use at the time of the examination, the device information obtained by said device information obtaining means includes at least one of a type name, a serial number, a use time, a number of uses, and a setting value of the devices used at the time of the examination; and recording means for recording information composing of the image information obtained by said image information obtaining means and the device information obtained by said device information obtaining means, as a single examination record.

8. A medical image recording system, comprising:

image information obtaining means for obtaining an observation image at the time of an examination for a medical treatment;

device information obtaining means for obtaining information of the image information obtaining means and information about a device being used while the device is connected to the image information obtaining means;

an identification information obtaining means for obtaining identification information about a non-connected examination device being used during the examination without being connected to the medical image recording system and while the non-connected examination device is in active use, and/or identification information about a drug used at the time of the examination; and recording means for recording the image information obtained by said image information obtaining means, the information about a device obtained by the device information obtaining means, and the information obtained by the identification information obtaining means, as a single examination record.

9. A medical image recording system, comprising:

image information obtaining means for obtaining an observation image at the time of an examination for a medical treatment;

device information obtaining means for obtaining information of the image information obtaining means and information of devices including at least one image capture device connected to the image information obtaining unit and at least one non-connected external device in active use in combination with the image capture devices used at the time of the examination, the device information obtained by said device information obtaining means includes at least one of a type name, a serial number, a use time, a number of uses, and a setting value of the devices used at the time of the examination;

image setting information obtaining means for obtaining setting information associated with an observation image the same time the observation image is obtained by said image information obtaining means; and recording means for recording information composing of the image information obtained by said image information obtaining means, the device information obtained by said device information obtaining means and the image setting information obtained by said image setting information obtaining means, as a single examination record.

10. A medical image recording system, comprising:

device information obtaining means for obtaining information of an image capture device and a non-connected external device in active use in combination with the image capture device used for an examination for a medical treatment at the time of the medical examination, the device information obtained by said device information obtaining means includes at least one of a type name, a serial number, a use time, a number of uses, and a setting value of the devices used at the time of the examination;

message determining means for determining contents of a message based on a type name within the device information obtained by said device information obtaining means;

display screen layout determining means for determining a display screen layout based on the type name of the device within the device information obtained by said device information obtaining means; and message displaying means for displaying the contents of the message determined by said message determining means according to the screen display layout determined by said display screen layout determining means.

11. The medical image recoding system according to claim 2, wherein the identification information obtaining unit reads identification information from an identification information recording unit disposed in the drug or device used at the time of examination.

12. The medical image recoding system according to claim 2, wherein the identification information obtaining unit is an RF-ID unit.

* * * * *